(12) United States Patent
Jenkins et al.

(10) Patent No.: US 9,499,852 B2
(45) Date of Patent: Nov. 22, 2016

(54) WOUND DRESSING

(75) Inventors: Andrew Tobias Jenkins, Bath (GB); Naig Tun Thet, Bath (GB); June Mercer-Chalmers, Bath (GB)

(73) Assignee: The University of Bath, Bath (GB)

( * ) Notice: Subject to any disclaimer, the term of this patent is extended or adjusted under 35 U.S.C. 154(b) by 0 days.

(21) Appl. No.: 14/371,275

(22) PCT Filed: Jul. 27, 2012

(86) PCT No.: PCT/GB2012/000625
§ 371 (c)(1),
(2), (4) Date: Dec. 16, 2014

(87) PCT Pub. No.: WO2013/104876
PCT Pub. Date: Jul. 18, 2013

(65) Prior Publication Data
US 2015/0111243 A1    Apr. 23, 2015

(30) Foreign Application Priority Data

Jan. 12, 2012  (GB) .................................. 1200490.9

(51) Int. Cl.
*C12Q 1/04* (2006.01)
*C12Q 1/14* (2006.01)
*A61K 49/00* (2006.01)

(52) U.S. Cl.
CPC ............ *C12Q 1/04* (2013.01); *A61K 49/0043* (2013.01); *A61K 49/0084* (2013.01); *C12Q 1/14* (2013.01)

(58) Field of Classification Search
None
See application file for complete search history.

(56) References Cited

U.S. PATENT DOCUMENTS

2002/0009488 A1    1/2002  Francis et al.

FOREIGN PATENT DOCUMENTS

| EP | 0613685 | 11/1998 |
|---|---|---|
| EP | 0639373 | 12/1998 |
| EP | 2361502 | 8/2011 |
| EP | 1897536 | 6/2012 |
| WO | 9920252 | 4/1999 |
| WO | 0115750 | 3/2001 |
| WO | 0126627 | 4/2001 |
| WO | 2005035012 | 4/2005 |
| WO | 2009020694 | 2/2009 |
| WO | 2010107533 | 9/2010 |
| WO | 2011000835 | 3/2011 |
| WO | PCT/GB2012/000625 | 7/2014 |

OTHER PUBLICATIONS

Chien-Chung, et al. (2011) "Dynamic Probing of Nanoparticle Stability In Vivo: A Liposomal Model Assessed Using In Situ Microdialysis and Optical Imaging", Journal of Nanomaterials, vol. 2011 (no issue), article ID 932719, 8 pages (1-8).*
Petrov, et al. (2009) "Thermally-Gated Liposomes: A Closer Look", Bioconjugate Chemistry, 20(5): 1037-43, author manuscript downloaded from NIH public access on Aug. 18, 2015.*
Lutwyche, et al. (1998) "Intracellular Delivery and Antibacterial Activity of Gentamicin Encapsulated in pH-Sensitive Liposomes", Antimicrobial Agents and Chemotherapy, 42(10): 2511-20.*
Senior et al, "Tissue distribution of liposomes exhibiting long half-lives in the circulation after intravenous injection" Biochemica et Biophysica Acta, (1985) 839(1), pp. 1-8.
Zhou, J. et al., "Development of a prototype wound dressing technology which can be detected and report colonization by pathogenic bacteria", Biosens. and Bioelec. (2011) 30, 67-72.
Zhou, J. et al., "A thin film detection/response system for pathogenic bacteria", J. Am. Chem. Soc. (2010) 132(18) pp. 6566-6570.
Arpigny, J.L., Jaeger, K.E., 1999. Biochem. J. 343, 177-183.
Bailey, C.J., Redpath, M.B., 1992. Biochem. J. 284, 177-180.
Branski, L.K. et al., 2009. Surg. Infec. (Larchmt) 10, 389-397.
Church, D. et al., 2006. Clin. Microbiol. Rev. 19, 403-434.
Dinges, M.M. et al., 2000. Clin. Microbiol. Rev. 13, 16-34.
Drulis-Kawa, Z., Dorotkiewicz-Jach, A., 2010. Int. J. Pharm. 387, 187-198.
Duncan, J.L., Buckingham, L., 1981. Biochim. Biophys. Acta. 648, 6-12.
FDA: Guidance for Industry (Chronic Cutaneous Ulcer and Burn Wounds—Developing Products for Treatment) Jun. 2006.
Garcia-Saez, A.J., Schwille, P., 2010. FEBS Lett. 584, 1653-1658.
Geny B. and Popoff, M.R. Biology of the Cell 98 (2006) 667-678.
Gilbert, R.J.C., Cellular and Molecular Life Sciences 59 (2002) 832-844.
Henna, O-.R. et al., 2002. Prog. In Lip. Res. 41, 66-97.
Hildebrand, A. et al., The Journal of Biological Chemistry 266 (1991) 17195-17200.
Holden, M.T.G. et al., 2004. Proc. Nat. Acad. Sci. USA. 101, 9786-9791.
Jelinek, R., Kolusheva, S., 2007. Top. Curr. Chem. 277, 155-180.
Jenkins, A.T.A. et al., 2011. Burns 37S, S5.
Jenkins, A.T.A., Young, A., 2010. Expe. Rev. of Anti-inf. Thera. 8, 1063-1065.
Jones, V.E., 2006. Wounds UK 2, 66-73.
Jones, M.N. et al., 1997. J. Drug Target 5, 25-34.
Laabei, M. et al., 2012. Pedia. Infect. Dis. J. 31, e73-e77.
Liu, S., et al., 2005. Langmuir 21, 8572-8575.
Liu, P.V., 1974. The. J. of Infec. Disea. 130, S94-S99.
Mateo, C.R. et al., 1995. Biophys. J. 68, 978-987.
Meers, M., et al., 2008. J. Antimicrobial Chemotherapy 61, 859-868.
National Burn Care Review (2001).
Nhung, D.T., et al., 2007. Int. J. Pharm. 334, 166-167.
Palmer, M., 2004. FEMS Microbiol. Lett. 238, 281-289.

(Continued)

*Primary Examiner* — Robert M Kelly
(74) *Attorney, Agent, or Firm* — Boulware & Valoir

(57) ABSTRACT

The invention provides vesicles that may be used in diagnosing infection, especially with infection by bacteria such as *Staphylococcus aureus* and *Pseudomonas aeruginosa*. The vesicles can be used in wound dressings.

6 Claims, 11 Drawing Sheets

(56) References Cited

OTHER PUBLICATIONS

Parish, C.R. Immunology and Cell Biology 77 (1999) 499-508.
Parker, M.W., and Feil, S.C., Progress in Biophysics and Molecular Biology 88 (2005) 91-142.
Peacock, S.J. et al., 2002. Infec. and Immu. 70, 4987-4996.
Poon, V.K.M. and Burd, A. Burns 30 (2004) 140-147.
Potrich, C. et al., 2009. J. Membrane Biol. 227, 13-24.
Raicu, P., Mixich, F., 1992. Mutat. Res. 283, 215-219.
Song, L. et al., 1996. Science 274, 1859-1866.
Songer, J.G., 1997. Tren. in Microbiol. 5, 156-161.
Tangpraphaphorn, S., 2004. Open. Compu. Fac., Uni. of California at Berkeley. PM527.
Thet, N.T. et al., 2011. Biosens. and Bioelec. 28, 227-231.
Thet, N.T., Jenkins, A.T.A., 2010. Electrochem. Comm. 12, 1411-1415.
Titball, R.W., 1993. Microbiol. Rev. 57, 347-366.
Tseng, C.W. et al., 2009. PLoS One, 4, e6387, 1-10.
UK Burn Injury Data (1986-2007).
Veatch, S.L., Keller, S.L., 2005. Biochim. et Biophys. Act. 1746, 172-185.
Verdon, J. et al., 2009. Peptides 30, 817-823.
Wasiak, J. et al., Cochrane Database of Systematic Reviews 2 (2009) 1-51.
Winsor, G.L. et al., 2009. Nucl. Aci. Res. 37, D483-D488.
Young, A.E., Thornton, K.L., 2007. Arch. Dise. Childh. Edu. Pract. Ed. 92, ep97-ep100.
Koyama, T.M. et al., 1999. The Chem. Edu. 4, 12-15.

\* cited by examiner

WOUND DRESSING

FIELD OF THE INVENTION

The invention relates to vesicles that may be used in diagnosing infection, especially with infection by bacteria such as *Staphylococcus aureus* and *Pseudomonas aeruginosa*. The vesicles can be used in wound dressings.

BACKGROUND TO THE INVENTION

Bacterial infection in wounds, especially burn-related wounds in children, is a major clinical problem in hospitals [D. Church et at (2006)]. Burn victims who are young children are particularly vulnerable to and at risk of infection due to immature immune systems, yet they are often a neglected patient group in the UK National Health Service (NHS) [Sir I. Kennedy (2010)]. In the UK, children under five years of age make up only 8% of the population but receive 53% of all serious scald burns with subsequent physiological and psychological effects [NBCR (2001)]. In general about 10% of all serious scald burns become infected, resulting in delayed healing, scarring, increased morbidity and mortality rates [UK Burn Injury Data (1986-2007)]. Burn wounds are different from other wounds, such as chronic wounds, in many aspects and therefore means of clinical diagnosis and treatment for wounds in general cannot be simply adopted for burn wounds [FDA (2006)]. Clinical symptoms of infection in burn wounds are very similar to the normal inflammatory response to a burn, and sepsis imposes difficulties in early detection of bacterial infection, thereby hindering effective treatment before the infection spreads uncontrollably [D. Church et al (2006)]. As a preventive measure to infection, paediatric burn victims are often treated with systematic antibiotics without concrete proof of a burn related 'actual' infection, thereby increasing healthcare antibiotic resistance. This has contributed to the evolution and increased resistance of pathogenic bacteria to the present day's antibiotics.

Current clinical treatment of burn wounds includes removal of debris, cleaning and application of a dressing, which effectively sterilises and seals the burn area [J. Wasiak et at (2009)]. This is followed by clinical observation and direct wound assessment for the possible initiation of infection as wound healing is in progress. Bacterial infection is still possible, though, if bacteria from the surrounding non-sterile skin enter the wound under the dressing. This is more likely to happen when direct wound assessment such as frequent removal and replacement of the dressing is required. Even if the burn wound is not infected, repeated changes of dressings extend the normal healing time, requiring a longer hospital stay and increasing the chance of scarring and trauma with additional concomitant costs. Hence, there is an urgent requirement for the ability to diagnose and identify burn wound infection, or absence thereof, without removal of expensive dressings. An alternative approach is the use of dressings impregnated with antimicrobial compounds such as silver ions for suppression of microbial growth. Despite the effectiveness of antimicrobials against bacteria, antimicrobial compounds such as silver may be partially cytotoxic to healthy cells and may also suppress tissue re-growth of wounds [V. K. M. Poon and A. Burd (2004)]. Importantly, continuous exposure of the wound to the antimicrobial agents is not a viable solution for preventive treatment of infection as this could increase the rate of evolution of bacteria resistance [A. T. A. Jenkins and A. E. Young (2010)].

Two main species of pathogenic bacteria commonly found in burn-related wound infections are *S. aureus* and *P. aeruginosa* [L. K. Branski et al. (2009)]. *S. aureus* is the gram-positive human pathogen persistently colonized on human skin flora. Most *S. aureus* strains are known to be pathogenic due to numerous secreted virulence factors including alpha, gamma and delta pore-forming toxins (PFTs), cholesterol binding toxins (CBTs) [R. J. C. Gilbert (2002)], and toxic shock toxins (TST) [M. M. Dinges et al. (2000) and S. Tangpraphaphorn (2004)]. TST is a major cause of toxic shock syndrome (TSS) Which functions by means of over-activation of the host immune system response. If not treated, TSS can cause death to the host within hours [A. E. Young and K. L. Thornton (2007), V. E. Jones (2006)]. The other principal agent, *P. aeruginosa*, is a gram-negative human opportunistic pathogen and is responsible for, amongst others, fatal infections in patients with cystic fibrosis and immuno-suppression [L. K. Branski et al. (2009)]. It is also found in human skin flora and is associated with various virulence factors for suspected lysis of healthy eukaryotic cells and tissue matrices upon infection. PFTs of *S. aureus* and lipid-degrading enzymes such as phospholipases of *P. aeruginosa* are proven to be able to lyse cell membranes or healthy cells in vivo and in vitro [J. G. Songer (1997), P. V. Liu (1974), M. M. Dinges et al (2000) and J. L. Arpigny and K. E. Jaeger (1999)]. Subject to the mode of action of particular lypolytic toxins of bacteria, pathogenic strains of *S. aureus* and *P. aeruginosa* were detected and discriminated from commensal *E. coli* bacteria by biomimetic lipid bilayer membrane on a gold surface using electrochemical impedance spectroscopy (EIS) and surface Plasmon resonance (SPR) [N. T. Thet and A. T. A. Jenkins (2010) and N. T. Thet et al (2011)]. A prototype wound dressing technology has been developed that can detect wound infection by pathogenic bacteria and alert clinicians automatically. It uses lipid vesicles containing fluorescent dyes attached to fabrics. [J. Zhou et al (2011)].

It would be particularly advantageous to be able to diagnose infection swiftly and simply, particularly if that diagnosis could identify the bacteria or type of bacteria responsible. Specifically, it would be advantageous to be able to identify the presence, or absence, of the bacteria most likely to cause infection in a burn wound, and to distinguish between these bacteria, if possible.

SUMMARY OF THE INVENTION

According to a first aspect of the invention, there is provided a vesicle comprising at least two of: 1,2-dipalmitoyl-sn-glycero-3-phosphocholine (DPPC), 1,2-dipalmitoyl-sn-glycero-3-phosphoethanolamine (DPPE), 1,2-distearoyl-sn-glycero-3-phosphocholine (DSPC); and 1,2-distearoyl-sn-glycero-3 phosphoethanolamine (DSPE); further comprising a sterol, especially cholesterol.

Preferably the vesicle encapsulates a signalling molecule.

The vesicle of the first aspect preferably comprises one of DPPC and DSPC. It also further comprises one of DPPE and DSPE. It preferably comprises DPPC and DPPE or DSPC and DSPE.

The vesicle preferably comprises between 0.5 and 10% DPPE or DSPE, especially between 1 and 5% DPPE or DSPE, most preferably 2% DPPE or DSPE. Including DSPE or DPPE in the vesicle is particularly useful as it allows the vesicle to immobilize onto surfaces, such as those used in wound dressings. In some embodiments, the DPPE and/or DSPE could be replaced by another lipid having the same chain length, but a different head group, such as DPPC, DSPC, DPPS, DSPS DPPI and DSPI.

The vesicle may also comprise sphingomyelin, in addition to or instead of the DPPE, DSPE, DPPS, DSPS, DPPI and DSPI. The vesicle may comprise up to about 18% sphingomyelin, but preferably comprises less than 10%, more preferably less than 5%.

The vesicle may additionally comprise 10,12-tricosadiynoic acid (TCDA) or other cross-linkable polymer lipids such as 10-undecenoic acid (UDA), and chromatic polymer polydiacetylene.

Particular embodiments of the first aspect of the invention follow. In those embodiments, whilst preferred components are defined, it is possible to replace DPPC with DSPC and DSPC with DPPC. It is also possible to replace DPPE with DSPE and DSPE with DPPE.

In a first embodiment of the first aspect, the vesicle preferably comprises DPPC, and a sterol, such as cholesterol. It preferably comprises between 40 and 75% DPPC and DPPE. More preferably, it comprises between 45 and 70% DPPC, more preferably between 50 and 65% DPPC, more preferably between 50 and 55% DPPC, most preferably 53% DPPC. It preferably also comprises between 0.5 and 10% DPPE, more preferably between 1 and 5% DPPE, most preferably 2% DPPE. It also preferably comprises between 15 and 25% sterol, especially cholesterol, more preferably between 17 and 23% sterol, most preferably 20% sterol. Further it preferably comprises between 5 and 30%, TCDA, more preferably between 10 and 30% TCDA, more preferably between 15 and 28% TCDA, more preferably between 22 and 28% TCDA, most preferably 25% TCDA. If the DPPC and DPPE in the vesicle types of the first aspect are replaced with DSPC and DSPE, the vesicle preferably comprises between 60 and 75% DSPC and between 5 and 20% TCDA.

In a second embodiment of the first aspect, the vesicle preferably comprises DSPC, and cholesterol. It preferably also comprises DSPE. It preferably comprises at least 70% DSPC and DSPE, more preferably at least 75%, even more preferably at least 77%. It preferably comprises between 70 and 85% DSPC, more preferably between 75 and 80% DSPC, most preferably 78% DSPC. It preferably comprises between 0.5 and 10% DSPE, more preferably between 1 and 5% DSPE, most preferably 2% DSPE. It further preferably comprises between 14 and 25% sterol, especially cholesterol, more preferably between 17 and 23% sterol, most preferably 20% sterol. It preferably does not comprise TCDA.

In a third embodiment of the first aspect, the vesicle preferably comprises DPPC, sterol, especially cholesterol, and TCDA. It preferably also comprises DPPE. It preferably comprises less than 35% DPPC and DPPE, more preferably less than 30%, even more preferably less than 27%. It preferably comprises between 15 and 30% DPPC, more preferably between 20 and 25%, most preferably 23% DPPC. It preferably comprises between 0.5 and 10% DPPE, more preferably between 1 and 5% DPPE, most preferably 2% DPPE. It further preferably comprises at least 40% sterol, especially cholesterol, especially between 45 and 55% sterol, more preferably between 47 and 53%, most preferably 50% sterol. It also preferably comprises between 20 and 30% TCDA, more preferably between 22 and 28% TCDA, most preferably 25% TCDA.

Concentrations are preferably % mol by volume.

A signalling molecule may be encapsulated in the vesicles. Any appropriate signalling molecule may be used. The signalling molecule is used to indicate rupture or lysis of the vesicle, the signal changing or display of the signal changing when the vesicle is ruptured. For example, the signalling molecule may be a dye or otherwise visualisable signalling molecule that can only be visualised when the vesicle is ruptured. The signal may be as simple as a colour being visible when vesicles are ruptured, such dyes are well known. Or it may be, for example, a fluorescent signal that requires illumination with UV light to be visible. Preferably the signalling molecule is a fluorescent dye, such as a fluorescein, especially 5(6)-carbo fluorescein.

Other possible signalling molecules include organic and inorganic dyes such as pH sensitive dyes such as crystal violet, bromothymol blue, methyl orange, calcein and other pH or concentration sensitive fluorometric dyes. Alternatively, other chemical signalling molecules, such as redox signalling molecules, may be encapsulated.

The vesicle may also encapsulate other molecules, especially active molecules, such as antibiotics, antimicrobials, bacteriophages or other biologically originating antimicrobials, and other biologically active agents.

The vesicles may also comprise lipids having different head groups, such as DSPI, DPPI, DSPS and DPPS.

Second and third aspects of the invention provide a composition and a wound dressing comprising at least one of the vesicles of the first aspect of the invention. Preferably, the composition or wound dressing comprises a plurality of such vesicles. Preferably the composition or wound dressing comprises vesicles according to the first embodiment of the first aspect. Alternatively, the composition or wound dressing may independently comprise vesicles according to the second embodiment, or to the third embodiment. Preferably, the composition or wound dressing may independently comprise vesicles according to more than one of the embodiments, especially according to the second and third embodiments.

Fourth and fifth aspects of the invention provide a composition and a wound dressing comprising first and second vesicles, the vesicles encapsulating a signalling molecule; wherein the first vesicle is sensitive to the presence of a first bacterium and the second vesicle is sensitive to the presence of a second bacterium.

The term "sensitive to" means that the vesicles may be lysed or ruptured by the bacteria.

In the fourth and fifth aspects of the invention, both the first and second vesicles are preferably sensitive to pathogenic bacteria, but not to non-pathogenic bacteria.

The definition of pathogenic bacteria compared with non-pathogenic bacteria depends on the location of bacteria on or in a person and the behaviour in a specific environment. In this context, pathogenic bacteria are bacteria that secrete virulence factors, such as toxins, that cause tissue damage. Pathogenic bacteria can cause harm to their eukaryotic hosts by secreting enzymes and toxins that damage cells and connective matrix material of the tissues. Many of these toxins and enzymes act as cell membrane-lysing and/or cell membrane-permeating agents.

*Staphylococcus aureus* has the following components and virulence factors:
  (i) Adhesins that allow it to attach to tissues.
  (ii) Enzymes such as nucleases, proteases, lipases, hyaluronidase, and collagenase that degrade tissue matrix proteins and allow deep tissue penetration.
  (iii) Toxins, such as $\alpha$, $\beta$, $\gamma$ and $\delta$-haemolysins, which can induce permeation of the cell membrane.
  (iv) Other virulence factors such as leukocidin, leukotoxin and exfoliative toxins act as cytotoxins, directly killing host cells, allowing further tissue invasion and suppressing the immune response and thus their own destruction.

(v) Exoproteins, such as toxic shock syndrome toxins, coagulase and protein A, act to further suppress the host immune system.

The secretion of virulence factors such as those mentioned is common to all pathogenic bacteria.

Pathogenic bacteria may be selected from the group comprising (but not limited to) *Salmonellae* species, *Shigellae* species, pathogenic *Escherichia coli* such as *E. coli* O157, *Staphylococcus*, in particular *S. aureus*, *Streptococcus*, in particular Group A and Group B *Streptococcus*, e.g. *S. pyogenes*, *S. agalactiae*, *Klebsiella* species, in particular *K. pneumoniae*, *Pseudomonas* species, in particular *P. aeruginosa*, *Lactobacillus*, *Helicobacter*, *Camphylobacter*, *Legionella*, *Listeria*, *Borellia*, *Yersinia*, *Bacillus* and *Vibrio*.

The membrane-permeating or membrane-lysing agents produced by pathogenic bacteria include lipases, phospholipases including phospholipase A2, toxic shock toxin (TSST-1), hyaluronidases, pore-forming toxins, in particular haemolysin, *S. aureus* a, b and d toxins, streptolysin and leukocidin.

In particular, the first vesicle type is preferably sensitive to gram-negative bacteria. The second vesicle type is preferably sensitive to gram-positive bacteria. The first vesicle type is preferably sensitive to *Pseudomonas* bacteria, especially *Pseudomonas aeruginosa*, especially strain PA01.

The first vesicle type preferably comprises a lipid bilayer made up predominantly of, that is to say comprising at least 60%, more preferably at least 70%, more preferably at least 75% lipids, even more preferably at least 80%, lipids comprising at least one, preferably two hydrophobic chains comprising at least 14 carbon atoms, more preferably comprising at least 16, most preferably at least 18 carbon atoms in each chain, resulting in the lipid bilayer being in a gel phase with little or limited fluidity at approximately 37° C. In particular, the lipid forming at least 60%, more preferably at least 70%, more preferably at least 75% lipids, even more preferably at least 80% of the lipid bilayer is preferably a glycerophosphocholine, especially a sn-glycero-3-phosphocholine, having two hydrophilic side chains, each comprising at least 14, more preferably at least 15, more preferably at least 16, more preferably at least 17, even more preferably at least 18 carbon atoms. Such side chains include palmitoyl, stearoyl and similar chains having the appropriate number of carbon atoms. The first vesicle type is preferably the vesicle according to the second embodiment of the first aspect of the invention.

The second vesicle type is preferably sensitive to *Staphylococcus* bacteria, especially *Staphylococcus aureus*, particularly strains that show reduced sensitivity or resistance to antibiotics. The second vesicle is most preferably sensitive to methicillinsensitive *Staphylococcus aureus* (MSSA), particularly strain MSSA476. The second vesicle type preferably comprises a lipid bilayer comprising less than about 40%, more preferably less than 35%, even more preferably less than 30% lipids comprising at least one, preferably two hydrophobic chains comprising at least 14 carbon atoms, more preferably comprising at least 16, most preferably at least 18 carbon atoms in each chain, resulting in the lipid bilayer being fluid at approximately 37° C. In particular, the lipid forming less than about 40%, more preferably less than 35%, even more preferably less than 30% lipids is preferably a glycerophosphocholine, especially a sn-glycero-3-phosphocholine, having two hydrophilic side chains, each comprising at least 14, more preferably at least 15, more preferably at least 16, more preferably at least 17, even more preferably at least 18 carbon atoms. Preferably the second vesicle type comprises at least 40%, more preferably at least 45% sterol, especially cholesterol. The second vesicle type is preferably the vesicle according to the third embodiment of the first aspect of the invention.

Accordingly, the composition or wound dressing preferably comprises two vesicle types, the first having a membrane in the gel phase and the second having a membrane in the fluid phase at around 35-40° C. That is to say, the composition or wound dressing preferably comprises a first vesicle type having a lipid bilayer with a first lipid transition temperature and a second vesicle type having a lipid bilayer with a second lipid transition temperature, wherein the first lipid transition temperature is higher than the second lipid transition temperature, preferably at least 5° C. higher, more preferably at least 8° C. higher, even more preferably at least 10° C.

As mentioned above, the vesicles may encapsulate a signalling molecule. In the composition of the second and fourth aspects, where different vesicle types are present, the vesicle types may encapsulate different signalling molecules, such that it is possible to identify which vesicles have been lysed. In the wound dressing of the third and fifth aspects, the different vesicle types may encapsulate different signalling molecules. Alternatively, they may encapsulate the same signalling molecule but be arranged in such a way that it is possible to identify which vesicles have been lysed. For example the vesicles may be arranged in separate areas in the wound dressing, or arranged to form a pattern.

The composition is preferably for topical application and may contain appropriate excipients or fillers required, or advantageous for, topical application. The composition may be an aqueous solution, comprising the vesicles, and be in liquid form. Alternatively, the composition may be a matrix of, for example, gelatin, pectin or a hydrogel or the like, also comprising the vesicles.

The wound dressing preferably comprises a support to which the vesicles are adhered. The support may be any appropriate support, such as a layer of fabric, especially a layer of polypropylene. The vesicles may be adhered in any appropriate way, such as using plasma-deposited maleic anhydride and UV photo-grafting of polyacrylic acid onto polypropylene to form covalent linkages to vesicles. Suitable methods for adhering the vesicles to the fabric are described in Liu et al., 2005. The wound dressing may comprise a matrix as described above, the dressing having for example a hydrogel or gelatin core, also comprising the vesicles, or on a support layer.

Also provided is a method of diagnosing an infection with a pathogenic bacterial strain, especially a *S. aureus* strain or a *P. aeruginosa* strain comprising contacting the infected area with vesicles according to the invention and observing the area for a signal from the signalling molecule.

The invention also provides the vesicles, compositions and wound dressings of the invention for use in therapy, especially for use in the diagnosis of a bacterial infection, especially an infection with *S. aureus* or *P. aeruginosa*, especially of wounds, particularly of burn wounds.

The invention also comprises a method of assessing the virulence of a bacterial strain, comprising contacting the strain with one or more vesicles of the invention and observing the vesicles for a signal from the signalling molecule.

Preferably the vesicles of the first embodiment of the aspect are used.

A signal from the signalling molecule is a sign or indicator that the vesicle has been ruptured and the signalling molecule released. For example, it could be a colour or fluorescence change or electrochemical signal.

The vesicles are sensitive to pathogenic bacteria but not to non-pathogenic bacteria, so can be used to distinguish between virulent and non-virulent strains. They can also give an indication of the virulence; a more virulent strain will produce a stronger signal from the signalling molecule than a less virulent strain.

When the composition comprises vesicles in a matrix, such as hydrogel or gelatin or pectin, the composition can be used as a model for human or animal tissue, in particular to predict the response of such tissue to an infective agent.

DETAILED DESCRIPTION OF THE INVENTION

The invention will now be described in detail by way of example only, with reference to the figures, in which.

Figure 4:
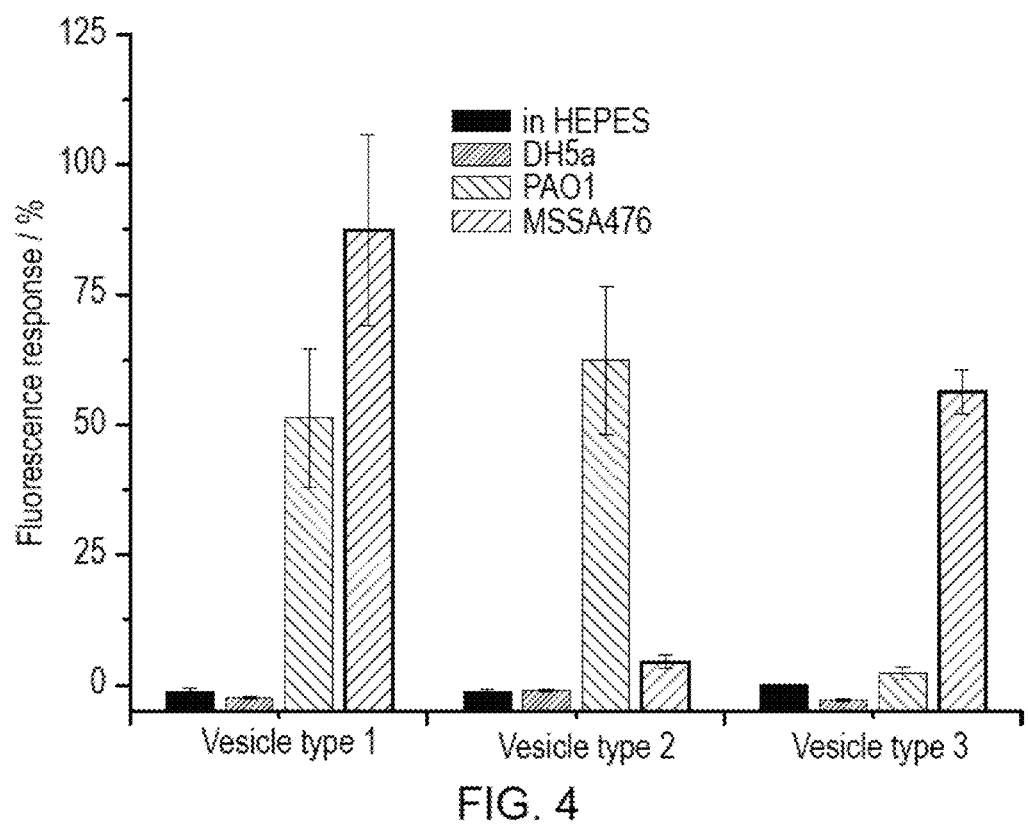
Figure 5:
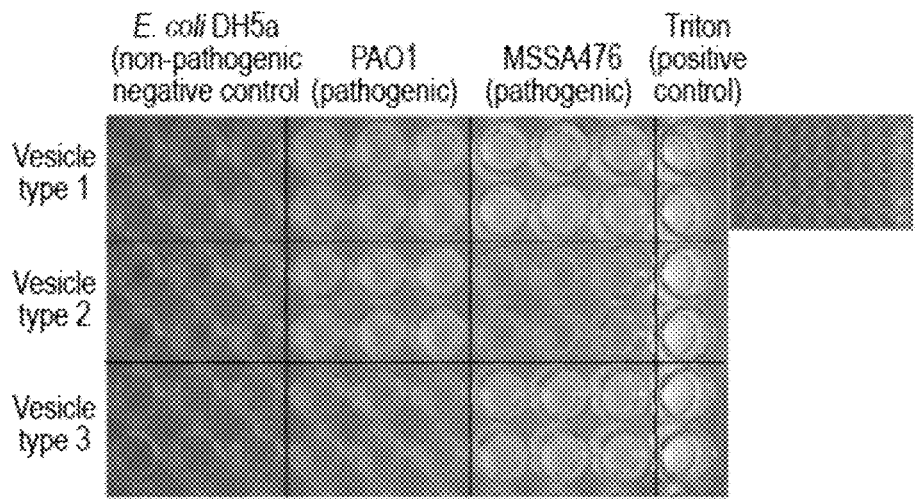

FIG. 4 shows the fluorescence response of vesicles type 1, 2 and 3 after 18 hours incubation of vesicles with bacteria containing growth media; and FIG. 5 shows the fluorescence switch on of vesicle type 1, 2 and 3 in 96 wells plate after 18 hours incubation of vesicles with bacteria containing growth media—vesicle type 1 shows fluorescence colour change to both PAO1 and MSSA476 but not to E. coli DH5α while vesicle type 2 and 3 show selective fluorescence colour change to PAO1 only and MSSA476 only respectively—negative control in HEPES is not shown in this image (inset on top right corner—96 wells plate at the beginning of incubation).

Figure 6A:
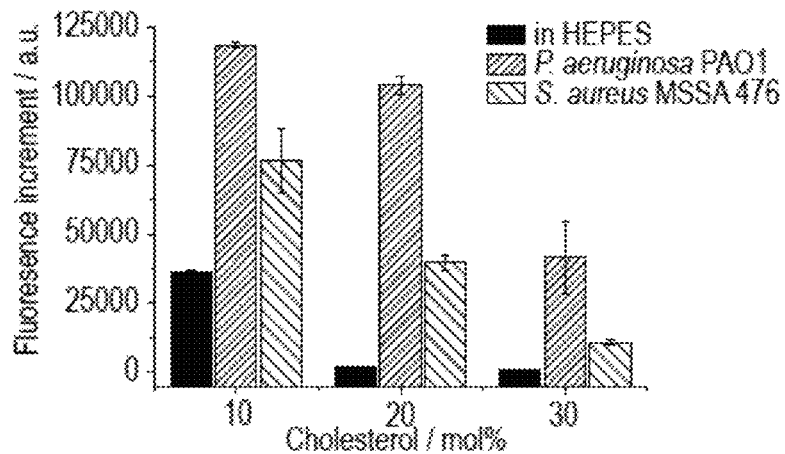
Figure 6B:
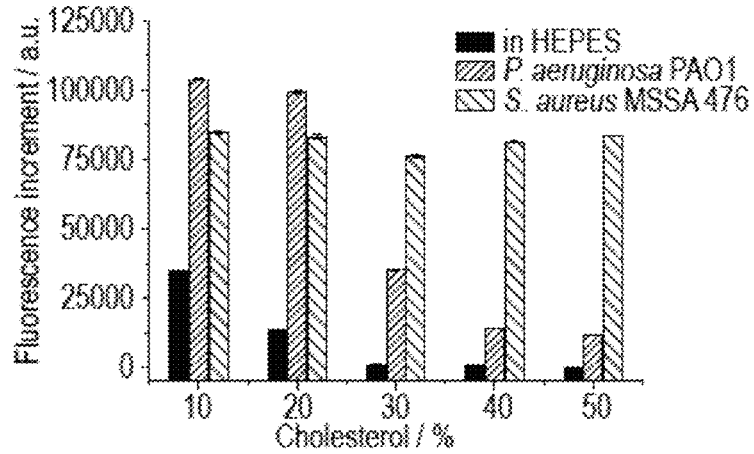
Figure 6C:
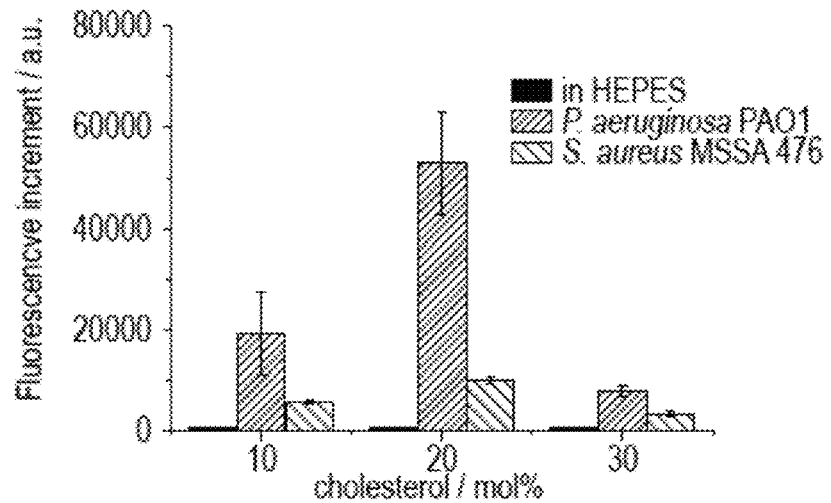
Figure 6D:
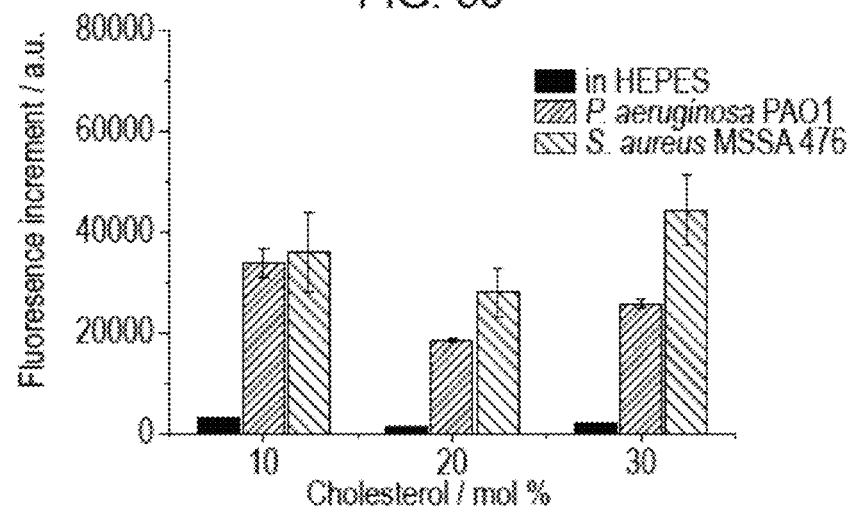

FIGS. 6a-d show the response of vesicle types A (FIG. 6a), B (FIG. 6b), C (FIG. 6c), E (FIG. 6d) to HEPES, PAO1 and MSSA476. FIG. 6a shows type A vesicles (1, 2, 3): DPPC with varying cholesterol concentration. FIG. 6b Type B vesicles (5, 6, 7, 8, 9): DPPC (TCDA 25 mol %) with varying cholesterol concentration. FIG. 6c shows type C vesicles (10, 11, 12): DSPC with varying cholesterol concentrations. FIG. 6d shows type E vesicles (17, 18, 19): DSPC (TCDA 25 mol %) with varying cholesterol concentration.

Figure 7:
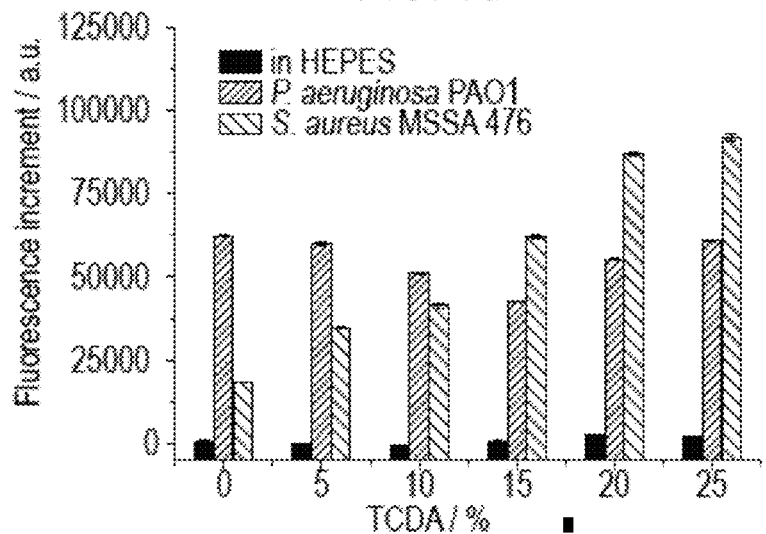

FIG. 7 shows the response of type D vesicles (12-17): DSPC (cholesterol 20 mol %) with varying TCDA concentration, to HEPES, PAO1 and MSSA476.

Figure 8A:
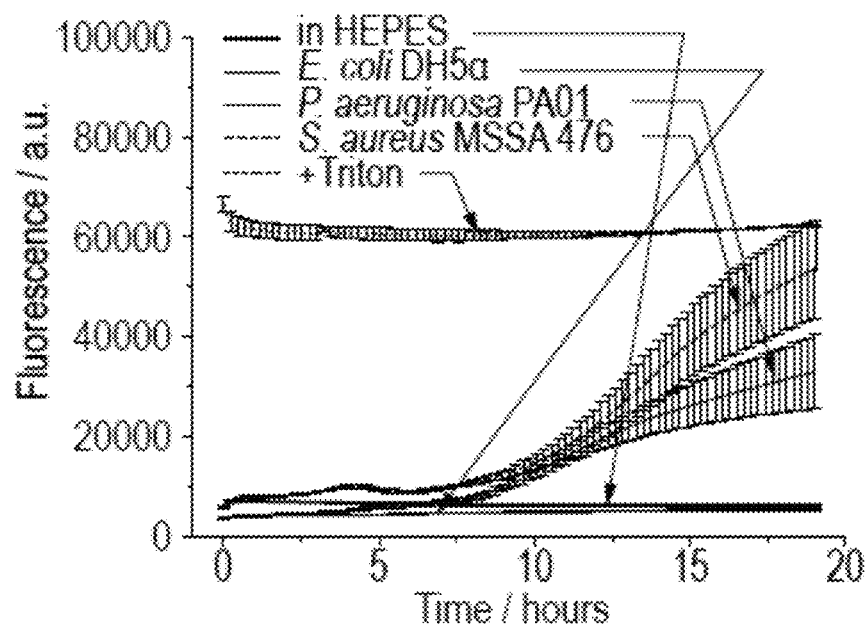
Figure 8B:
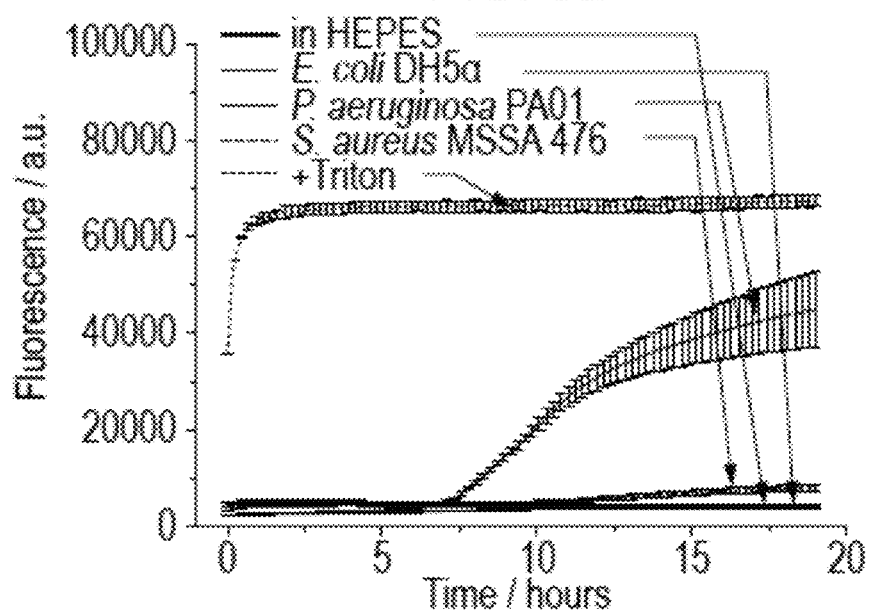
Figure 8C:
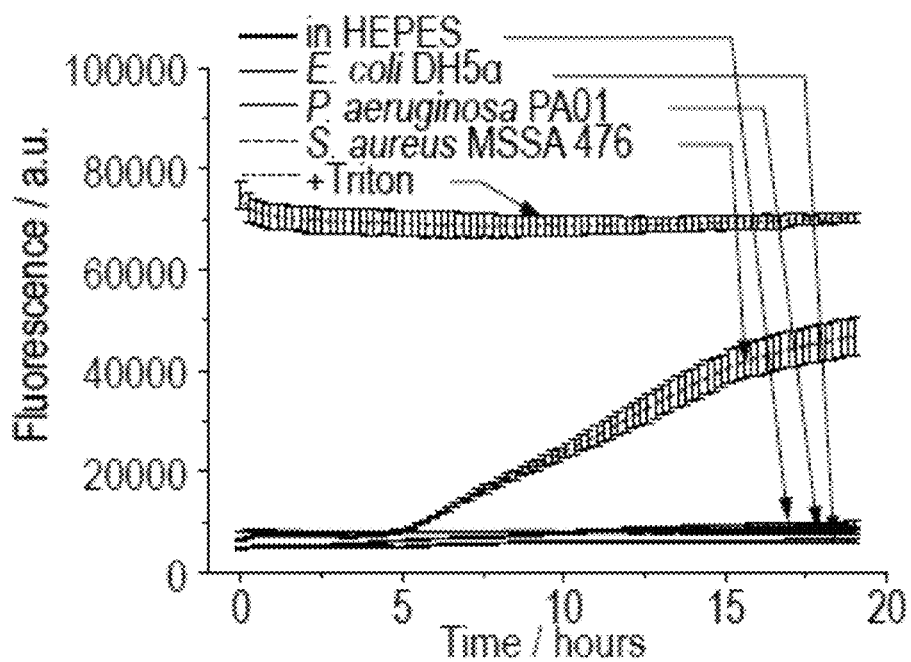
Figure 8D:
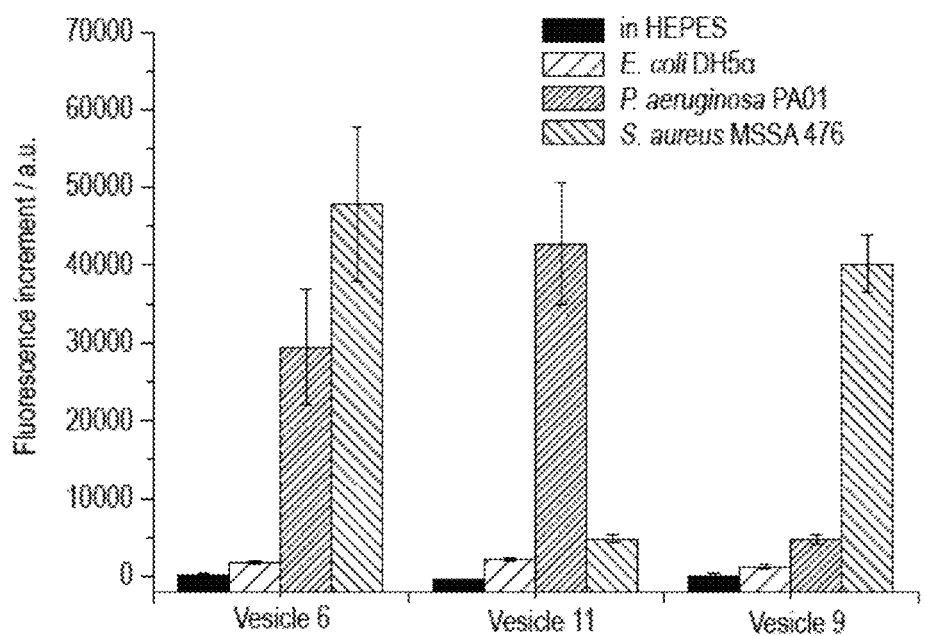

FIG. 8a-d shows the response of vesicles 6, 9 and 11 to HEPES, PAO1, MSSA476 and E. coli. FIG. 8a shows that vesicle 6 responds to both P. aeruginosa PAO1 and S. aureus MSSA 476 FIG. 8b shows that vesicle 11 only responds to P. aeruginosa PAO1. FIG. 8c shows that vesicle 9 only responds to S. aureus MSSA476 and FIG. 8d shows that none of vesicles 6, 9 and 11 responds to non-pathogenic E. coli DH5α.

Figure 9:
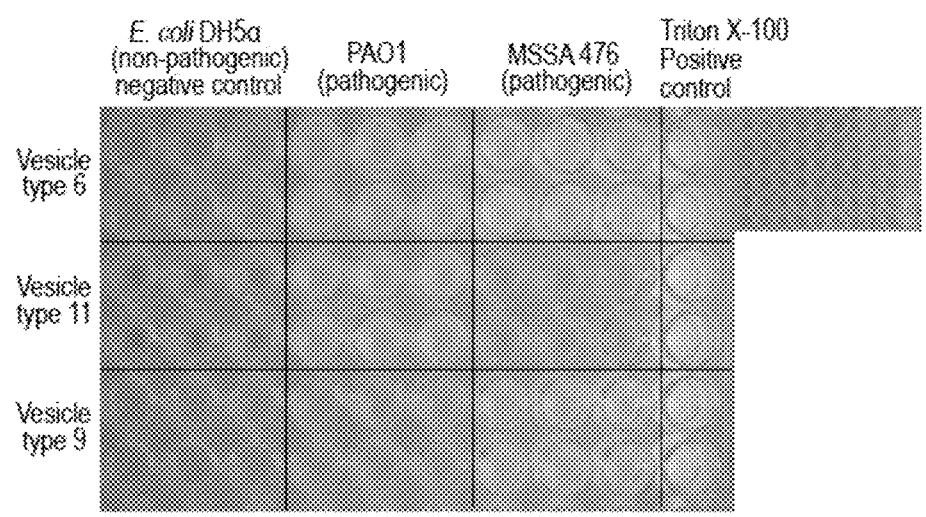

FIG. 9 shows colorimetric selectivity of vesicles 6, 9 and 11 between non-pathogenic E. coli DH5α and pathogenic strains of P. aeruginosa PAO1 and S. aureus MSSA 476 in 96 wells plate assay.

Figure 10A:
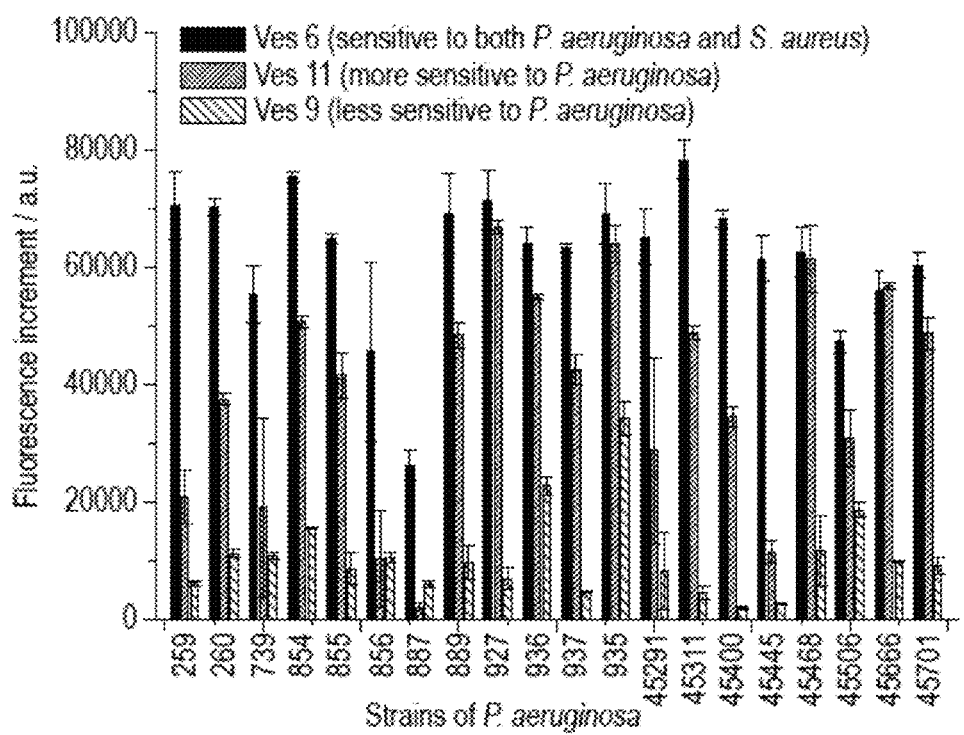
Figure 10B:
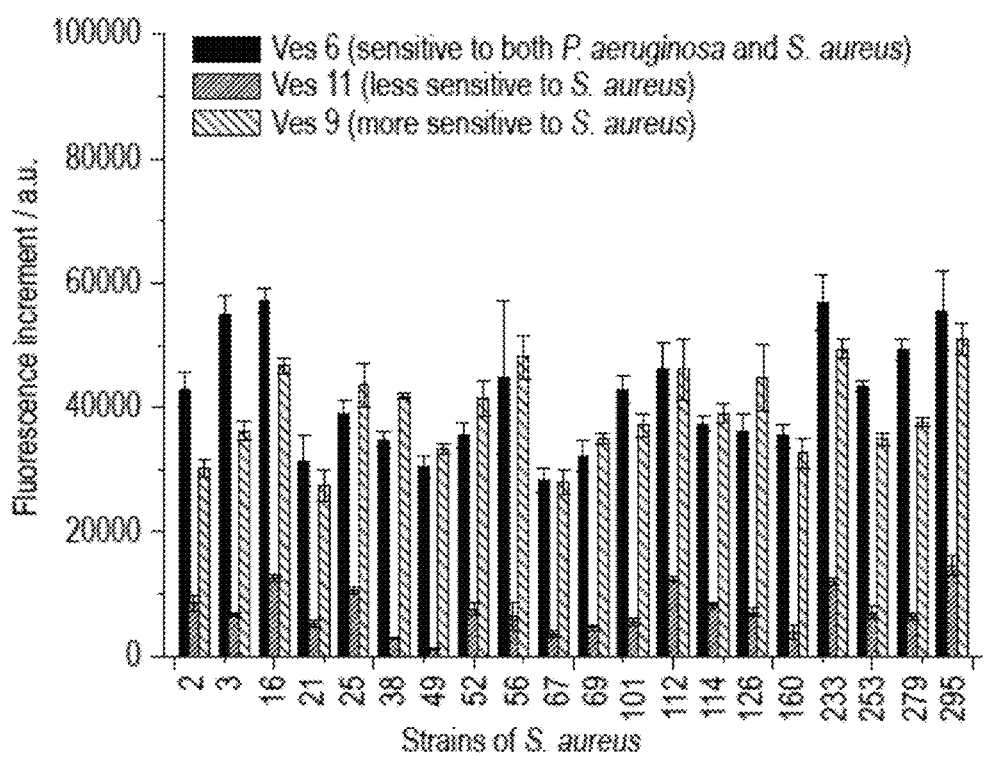

FIG. 10 shows the results of a comparison of the selectivity of vesicles 9 and 11 for various strains of S. aureus and P. aeruginosa.

EXAMPLES

Example 1

Materials and Methods
Materials and Making of Vesicles

Lipids used in making the vesicles are 1,2-dipalmitoyl-sn-glycero-3-phosphocholine (DPPC), 1,2-dipalmitoyl-sn-glycero-3-phosphoethanolamine (DPPE), 1,2-distearoyl-sn-glycero-3-phosphocholine (DSPC) and 1,2-distearoyl-sn-glycero-3-phosphoethanolamine (DSPE), all purchased from Avanti Polar Lipids, USA. 99.99% purity biological grade cholesterol, 10,12-tricosadiynoic acid (TCDA) and 5(6)-carboxyfluorescein were directly purchased from Sigma-Aldrich, UK. Cholesterol is a key component in cell membranes of eukaryotic cells. Cholesterol not only has a profound effect on regulation of cell membrane fluidity [T. M. Koyama et al (1999)] but also plays an important role in interaction with bacterial toxins [M. Plainer (2004)]. TCDA (a synthetic polymerizable lipid) is used to stabilize the vesicles, by lateral cross-linking within the lipid bilayer after UV exposure, in a partially dehydrated condition. 5(6)-carboxyfluorescein is a fluorescent dye with excitation and emission wavelengths of 495 and 520 nm respectively. It is encapsulated inside the lipid vesicles. 5(6)-carboxyfluorescein has been widely used as a tracer agent in molecular biology and to track the cell division, migration and proliferation in both in vitro and in vivo studies [C. R. Parish, 1999]. All the lipids, cholesterol and TCDA were used without further purifications. Triton X-100, available from Sigma-Aldrich, UK is a non-ionic detergent that disintegrates and reduces the lipid vesicles into micelles with simultaneous release of encapsulated carboxyfluoresceins. It was diluted 10 times in MilliQ water and used as a positive control during plate reading assay experiments. HEPES buffer was prepared according to standard protocol and used as a negative control for the stability of vesicles in the absence of bacteria and Triton X-100.

In vesicle preparation, lipids, cholesterol and TCDA were individually mixed in chloroform to 100 mmol dm$^{-3}$. They are then mixed together to a desired composition, utilising a 100 ul volume of each component, and dried under nitrogen before being placed in a vacuum chamber at 10$^{-3}$ bar for an hour, to remove solvent residues. Thoroughly dried lipid mixture was then rehydrated in 5 ml HEPES buffer, at pH 7.3, containing 50 mmol dm$^{-3}$ carboxyfluorescein. After thorough remixing in HEPES, the lipid solution was heated in a hot water bath at 75° C. for 10 minutes before being subjected to three repeated cycles of rapid freeze (in liquid nitrogen) and thaw (in the hot water bath). The lipid solution was then extruded three times through a polycarbonate membrane, of 100 nm diameter pore size, using a Lipofast extruder (Avestin, USA). Finally, the extruded vesicles were purified through a DNA grade Sephadex G-25 column (GE Healthcare, UK) in HEPES buffer, to separate vesicles from un-encapsulated carboxyfluorescein dye. Lipid vesicles containing TCDA lipids (1 ml, at a time in a quartz vial) were exposed to UV-light (254 nm) for a total of 12 seconds in a commercial flood exposure UV source (Hamamatsu, Japan), having been stored at 4° C. for at least two hours prior to UV exposure.

Type of Vesicles

All the vesicles were fabricated from 100 mmol dm$^{-3}$ of freshly prepared lipid stocks in 99.99% purity chloroform. The mixing ratio of lipids, cholesterol and TCDA in each type of vesicle is given in % volume. Vesicle type 1 is composed of 53% DPPC, 2% DPPE, 20% cholesterol and 25% TCDA. Vesicle type 2 contained 78% DSPC, 2% DSPE and 20% cholesterol, while vesicle type 3 was prepared with 23% DPPC, 2% DPPE, 50% cholesterol and 25% TCDA. Vesicle types 1 and 3 required UV cross-linking as they contained TCDA lipids. After extrusion and UV cross-linking, all the vesicles were stored at 4° C. until such time as they were utilised in experiments.

Microbial Culture

Pathogenic bacteria used in this study were:
1) Clinically isolated, gram-positive strain Methicillin-sensitive *S. aureus* (MSSA476) [M. T. G. Holden et al (2004)];
2) Clinically significant, gram-negative strain of *P. aeruginosa* (PAO1) [G. L. Winsor et al (2009)]; and
3) A lab strain (non-pathogenic) *E. coli* (DH5α), used as a control, with most virulence factors removed.

Bacterial cultured LB and TSB media were prepared in MilliQ water according to the standard ratio and procedure, followed by immediate autoclaving prior to use. DH5α and PAO1 were grown in LB media. MSSA476 was cultured in TSB medium. Bacteria were cultured in tubes containing 10 ml of broth held in a shaking incubator at 37° C. for 16 hours. The optical density (OD) of cultured bacteria was measured, at 600 nm in absorbance mode, before and after dilution. OD of bacteria was then related back to the colony-forming unit per mil (CFU/ml) by a conventional plating and counting method. Initial concentration of bacteria to be tested with vesicles was in the range of $10^2$ and $10^3$ CFUml$^{-1}$.

Plate Reading Assay

Figure 1:
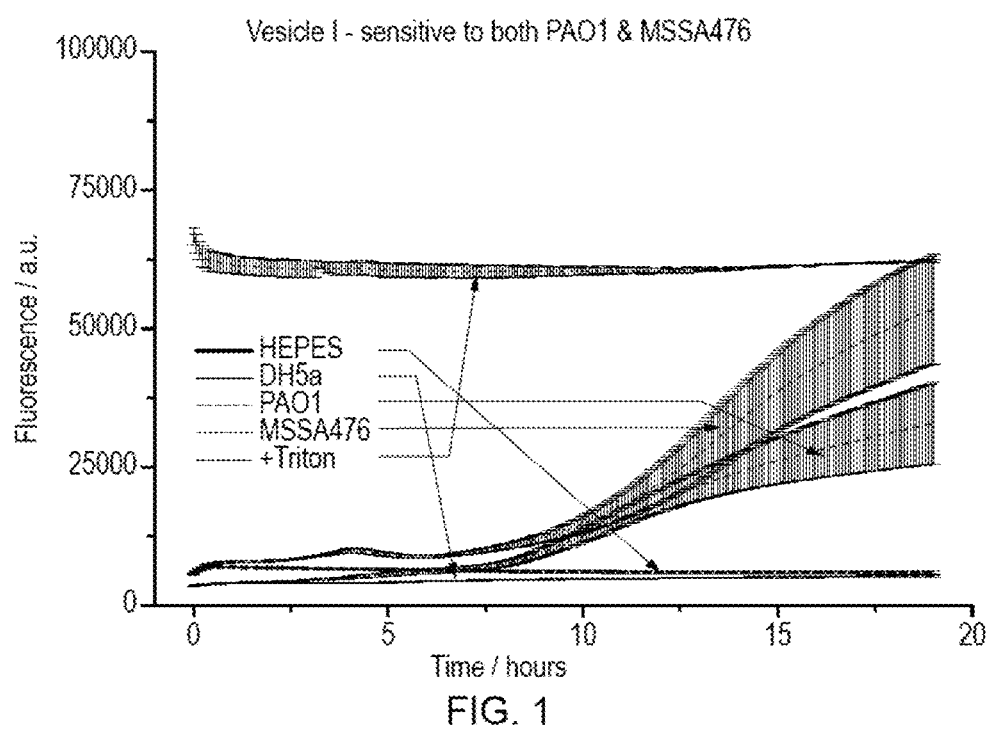
FIG. 1 shows the fluorescence response of vesicle type 1 upon inoculation of vesicles with E. coli DH5α, PAO1 and MSSA476 bacteria in respective growth media—vesicles in HEPES buffer is the negative control and vesicles+Triton X-100 is the positive control.

A BMG Labtech Fluorostar plate reading fluorimeter with a 96 well plate, in fluorescence mode with excitation and emission wavelengths of 495 nm and 520 nm respectively, was used to measure the time-dependent fluorescence response of vesicles during incubation with growing bacteria. In an individual well, 50 ul of each vesicle solution was inoculated with 100 ul of diluted broth-containing bacteria. Experiments were repeated 6 times for each vesicle type and bacteria combination. 100 μl of HEPES and diluted Triton X-100 were added into each type of vesicle, as negative and positive controls respectively. Fluorescence responses of lipid vesicles inoculated with bacteria, HEPES and Triton X-100 were continuously measured at 37° C. for 18 hours. For each type of vesicle and bacterial combination, the average and standard deviation of fluorescence release of 6 repeated measurements were used to calculate the fluorescence response, using the equation below:

$$\% \text{ fluorescence response} = \frac{F_{final} - F_{initial}}{F_{Triton} - F_{initial}} \times 100 \quad 1.1$$

where $F_{final}$=average fluorescence with bacteria/HEPES after 18 hours
$F_{initial}$=average fluorescence with bacteria/HEPES at the beginning
$F_{Triton}$=average fluorescence with Triton X-100 after 18 hours Results and Discussion With an initial bacterial concentration in broth of $10^2 \sim 10^3$ CFU ml$^{-1}$, it took an average of 6 hours before a fluorescence response was observed. As a positive control, Triton X-100 was utilised to lyse all vesicles, giving a 100% response with maximum release of fluorescence molecules (FIG. 4). Vesicle type 1 gave a clear response to both PAO1 and MSSA476 with visible fluorescence switch-on when observed under UV light (FIG. 5). Upon completion of the experiment, a fluorescence response of approximately 50% to PAO1 and 80% to MSSA476 was observed with vesicle type 1 (FIG. 1). The response to PAO1 was slightly lower than that to MSSA476. In comparison, the response to the negative control, HEPES, and the non-pathogenic *E. coli* DH5α that gave almost no fluorescence release, the responses to both PAO1 and MSSA476 were clearly visible and distinguishable (FIG. 5). This demonstrated the selective response of vesicle type 1 to pathogenic PAO1 and MSSA476 but not to non-pathogenic *E. coli* DH5α (FIG. 1).

Figure 2:
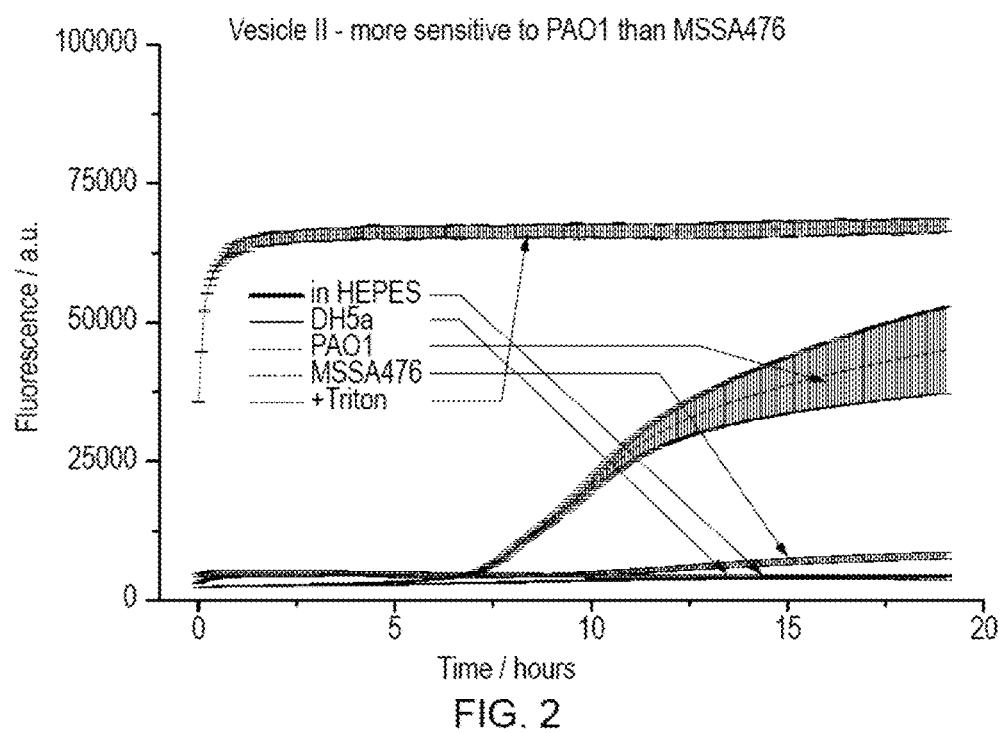
FIG. 2 shows the fluorescence response of vesicle type 2 upon inoculation of vesicles with E. coli DH5α, PAO1 and MSSA476 bacteria in respective growth media.

Vesicle type 2 gave an approximately 65% response to PAO1 with a less than 10% response to MSSA476, thus exhibiting 6.5 fold sensitivity to PAO1 with respect to MSSA476 (FIG. 2). A fluorescence response of less than 10% was not really detectable and noticeable with respect to the above 60% response, hence there was a clear difference in fluorescence visibility between the wells containing PAO1 and those containing MSSA476 (FIG. 4). The majority of toxins produced by *P. aeruginosa* are lipid-degrading extracellular enzymes such as phospholipases in addition to some endotoxins mainly associated with the outer cell membrane of gram-negative bacteria [J. G. Songer (1997)]. Bacterial phospholipases are very site specific and known to target the major lipids of a eukaryotic cell membrane including phosphatidylcholine (PC) and phosphatidylethanolamine (PE) [R. W. Titball (1993)]. Different bacterial phospholipases specifically recognize the target lipids and are capable of hydrolysing lipids by catalysis action. Phospholipids hydrolyzed by phospholipases are first reduced to lysophospholipids, followed by the subsequent removal of the fatty acid head groups from lipids. Overall, this results in the gradual lipid loss out of the cell membrane and the cell membrane disintegrates upon persistent hydrolysis of lipids by phospholipases.

Vesicle type 2 was designed to contain 80% of DSPC and DSPE and these lipids most likely became primary targets of extracellular enzymatic toxins of PAO1. This mechanism is the likely basis of the sensitivity to PAO1 demonstrated by vesicle type 2 sensitive. Gram-positive *S. aureus* pathogen is known to secrete various virulence factors, including extracellular diffusible protein toxins such as alpha, gamma and delta haemolysins, enterotoxins, leukocidins [M. W. Parker and S. C. Feil (2005)] and toxic shock syndrome toxins (TSST) [M. M. Dinges et al (2000)]. Haemolysins are pore forming toxins (PFTs) and able to form heptameric pores in cell membrane which are hydrophilic and non-specific to ions and charged molecular transports [L. Song et al (1996) and A. Hildebrand et al (1991)]. In the haemolysis of cell membranes in vivo, haemolysin pores interrupt the electrochemical potential gradient across the cell membrane, leading to uncontrolled permeation of ions in and out of the cell, and the premature death of cells occurs by lysis such as apoptosis or necrosis [B. Geny and M. R. Popoff (2006)]. Primary requirements for haemolysin monomers to bind onto cell membranes are: free availability of lipid head groups and sufficient fluidity of lipid membrane [J. Verdon et al (2009)]. A lipid bilayer made of lipids with more than 14 carbon atoms in the hydrocarbon chains is in the gel phase at 37° C., thus not fluid enough to allow the monomer insertion, and can also not provide the free lipid head groups for successful binding of monomers [T. M. Koyama et al (1999)]. Vesicle type 2 is primarily made of DSPC and DSPE lipids with 18 carbon atoms in their hydrophobic chains, and hence the lipid bilayer is almost in gel phase with little or limited fluidity at the experimental temperature of 37° C. This made the binding of exotoxins of MSSA476 to the lipid bilayer ineffective. Consequently type 2 vesicles were relatively stable in the presence of MSSA476 (FIG. 2). Hence, vesicle type 2 exhibited much higher sensitivity to PAO1 than to MSSA476 (FIG. 4).

Figure 3:
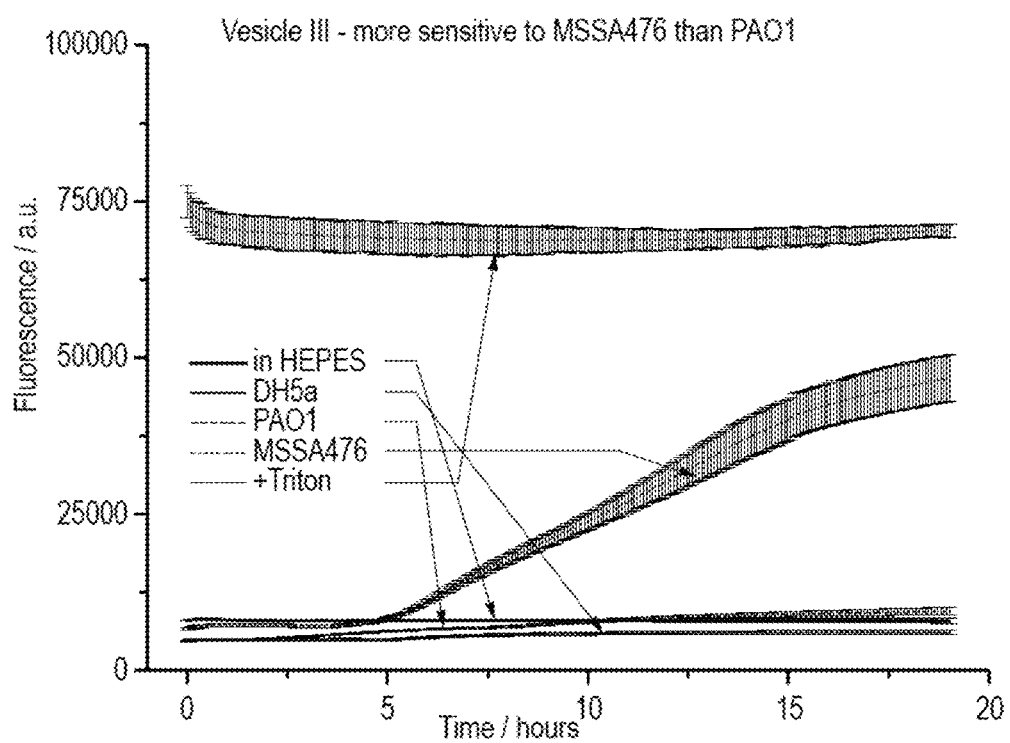
FIG. 3 shows the fluorescence response of vesicle type 3 upon inoculation of vesicles with E. coli DH5α, PAO1 and MSSA476 bacteria in respective growth media.

Vesicle type 3 showed an approximate 60% response to MSSA476 with less than 10% response to PAO1, and visible switch on only for MSSA476, as shown in FIG. 4. Vesicle type 3 was composed of DPPC, DPPE, cholesterol and TCDA. Phospholipids DPPC and DPPE made up 25% of the membrane composition, along with 50% cholesterol and 25% TCDA. This composition ensures the maintenance of sufficient membrane fluidity, primarily due to the high cholesterol concentration. The fluidity of the membrane enabled the exotoxins of MSSA476 to insert and exert toxin activities such as pore formation. Additionally, cholesterol-rich lipid bilayer membranes are more susceptible to interactions with bacterial toxins such as CBTs [M. Palmer (2004) and R. J. C. Gilbert (2002)]. Consequently the lipid bilayer of vesicle type 3 was substantially more vulnerable to the toxins of MSSA476 than those of PAO1 and thus exhibited relatively higher sensitivity to MSSA476 (FIG. 3). PAO1, on the other hand, primarily requires lipids to activate most of its lipid-degrading enzymes and endotoxins. With the minimal lipid composition of DPPC and DPPE in vesicle type 3, activation of PAO1 toxins was mostly ineffective in a lipid membrane dominated by cholesterol and TCDA lipids. As a result, vesicle type 3 was much less sensitive to PAO1 than MSSA476 (FIG. 4). It was observed that all types of vesicles inoculated in HEPES and *E. coli* DH5α showed no fluorescence response, indicating the effective selectivity of all vesicles between pathogenic and non-pathogenic bacteria tested in this experiment (FIG. 5).

Conclusion

The inventors have demonstrated the selective detection between non-pathogenic bacteria *E. coli* DH5α and pathogenic bacteria of *S. aureus* MSSA476 and *P. aeruginosa* PAO1 using fluorescent dye-encapsulated lipid vesicles. There is a clear visual distinction between pathogenic and non-pathogenic strains of bacteria, in the form of fluorescence colour switch-on to bright green, after inoculation of bacteria with lipid vesicles and incubated at 37° C. By formulating the appropriate compositions of lipids, cholesterol and polymer lipids, the vesicles have exhibited selective sensitivity between two pathogenic strains of bacteria, PAO1 and MSSA476. By integration of self-responsive lipid vesicles into a wound dressing, the current selective and discriminative sensing system has potential for future use as a rapid indicator of possible burn wound infections, without requiring the removal of the wound dressing throughout the wound healing process.

Example 2

Materials and Methods

Materials and Making of Vesicles

Vesicles employed in this study were prepared from the following lipids: 1,2-dipalmitoyl-sn-glycero-3-phosphocholine (DPPC), 1,2-dipalmitoyl-sn-glycero-3-phosphoethanolamine (DPPE), 1,2-distearoyl-sn-glycero-3-phosphocholine (DSPC) and 1,2-distearoyl-sn-glycero-3-phosphoethanolamine (DSPE) supplied by Avanti Polar Lipids, USA. Cholesterol, 10,12-tricosadiynoic acid (TCDA) and 5(6)-carboxyfluorescein were obtained from Sigma-Aldrich, UK. TCDA is a synthetic polymerizable lipid, used to stabilize the vesicles by lateral cross-linking within the lipid bilayer after exposure to UV light. The lipids, cholesterol and TCDA were used without further purification. Triton X-100 (Sigma-Aldrich, UK), a non-ionic detergent which solubilises, disintegrates and reduces the lipid vesicles into micelles with simultaneous release of encapsulated carboxyfluoresceins, was diluted 10 fold in MilliQ water (107 mg/ml) and used as a positive control during plate reading assay experiments. HEPES buffer was prepared according to standard protocol and used as a negative control for the stability of vesicles in the absence of bacteria and Triton X-100.

In vesicle preparation, lipids, cholesterol and TCDA were individually made up in chloroform to a volume of 100 mmol dm$^{-3}$. They were then combined to the desired composition in 100 μl and dried under nitrogen before being placed in a vacuum chamber at 10$^{-3}$ bar for an hour, to remove residual solvent. The dried lipid mixture was then rehydrated in 5 ml of HEPES buffer, at pH 7.3, containing 50 mmol dm$^{-3}$ carboxyfluorescein. After rehydration, the lipid solution was heated in a hot water bath at 75° C. for 10 minutes before being subjected to three freeze-thaw cycles. The lipid solution was then extruded three times through a 100 nm diameter pore size polycarbonate membrane using a LF-50 Lipofast extruder (Avestin, USA). Finally, the extruded vesicles were purified through a DNA grade Sephadex G-25 column (GE Healthcare, UK) in HEPES buffer to separate the vesicles from any un-encapsulated carboxyfluorescein dye. After storage at 4° C. for at least two hours the TCDA-containing lipid vesicles were placed in quartz vial and exposed to UV-light (254 nm) for a total of 12 seconds in a commercial flood exposure UV source (Hamamatsu, Japan).

TABLE 1

Vesicle types, with mol % of their phospholipid/fatty acid content (Arbitrary classification A-E depending on principal lipid component and variable i.e. cholesterol or TCDA; vesicle 17 belongs to both type D and E, and vesicle 11 belong to both type C and D).

| | | Vesicles (Types and lipid compositions in mol %) | | | | Fluorescent increment (average) in response to bacteria (a.u.) | | |
|---|---|---|---|---|---|---|---|---|
| Class | Vesicle Types | DPPC | DSPC | Cholesterol | TCDA | Hepes (buffer) | PAO1 | MSSA 476 |
| A | Ves 1 | 88 | — | 10 | — | 37500 | 115000 | 75000 |
| | Ves 2 | 78 | — | 20 | — | 1000 | 100000 | 37500 |
| | Ves 3 | 68 | — | 30 | — | 1000 | 37500 | 12500 |
| B | Ves 4† | 73 | — | 0 | 25 | 50000 | 105000 | 75000 |
| | Ves 5† | 63 | — | 10 | 25 | 37500 | 102000 | 76000 |
| | Ves 6*† | 53 | — | 20 | 25 | 12500 | 97000 | 72000 |
| | Ves 7† | 43 | — | 30 | 25 | 1000 | 35000 | 69000 |
| | Ves 8† | 33 | — | 40 | 25 | 1000 | 13000 | 73000 |
| | Ves 9*† | 23 | — | 50 | 25 | 1000 | 11000 | 78000 |
| C | Ves 10 | — | 88 | 10 | — | 500 | 20000 | 10000 |
| | Ves 11* | — | 78 | 20 | — | 550 | 55000 | 11000 |
| | Ves 12 | — | 68 | 30 | — | 200 | 12500 | 5000 |
| D | Ves 13† | — | 73 | 20 | 5 | 500 | 60000 | 35000 |
| | Ves 14† | — | 68 | 20 | 10 | 450 | 50000 | 40000 |
| | Ves 15† | — | 63 | 20 | 15 | 500 | 42500 | 62500 |
| | Ves 16† | — | 58 | 20 | 20 | 550 | 52500 | 85000 |
| | Ves 17† | — | 53 | 20 | 25 | 400 | 35000 | 37000 |
| E | Ves 18† | — | 63 | 10 | 25 | 200 | 20000 | 30000 |
| | Ves 19† | — | 43 | 30 | 25 | 300 | 25000 | 45000 |

Note:
*Vesicles used for selective sensitivity tests.
†Vesicles required UV cross-linking.
All DPPC and DSPC vesicles contain 2 mol % of DPPE and DSPE respectively.

Types of Vesicles

In order to elucidate the role of the various components with respect to vesicle sensitivity towards different bacteria, five classes of vesicles were studied (A-E in table 1), each with one component being varied. Type A vesicles were primarily shorter chain DPPC, with cholesterol varied between 0-30 mol %; Type B were similar to Type A with inclusion of a photopolymerizable component TCDA; Type C were longer chain DSPC lipids with varying cholesterol concentrations; Type D were DSPC based, had fixed cholesterol concentrations and varying TCDA concentrations; Type E included DSPC with fixed TCDA concentrations and varying cholesterol concentrations.

The rationale of this study design being that variation in cholesterol, lipid chain length and TCDA concentrations profoundly affect membrane properties such as fluidity and phase transition temperature, which in turn have significant effects on membrane interaction with bacteria and toxins (Potrich et al., 2009).

Pathogenic Bacteria and their Culture

A total of 21 clinical strains of pathogenic *S. aureus* were provided by the John Radcliffe Hospital, Oxford, UK; 19 strains of these were Methicillin sensitive *S. aureus* (MSSA) and the remaining 2 were Methicillin resistant *S. aureus* (MRSA). All MSSA and MRSA candidates studied in this work were community acquired virulent strains with suspected virulence factors that were susceptible to cell lysis (Peacock et at, 2002). As a counterpart to the *S. aureus* strains with respect to selective sensitivity, we examined 21 clinical strains of *P. aeruginosa* provided by Ampliphi Biosciences Corporation, UK and Southmead Hospital, Bristol, UK. Eight strains of *P. aeruginosa* acquired from Southmead Hospital were extracted from either acute wounds or from blood agar of infected patients. The remaining 13 strains were clinical extracts from chronic wounds with known pathogenic effects on human hosts. All the strains studied in this work were tabulated in table 2. The DH5α strain of *E. coli*, a laboratory strain with most of virulence factors removed, was employed as a non-pathogenic control (Hanahan, 1985).

TABLE 2

Bacterial strain types used for selective sensitivity study in this work.

| Species | Strain numbers | Remarks |
|---|---|---|
| S. aureus | 2, 3, 16, 21*, 25, 38, 49, 52, 56, 67, 69*, 101, 112, 114, 126, 160, 233, 253, 279, 295, 476 | *MRSA strains Remaining are MSSA strains. |
| P. aeruginosa | 259, 260, 739, 854, 855, 856, 887, 889, 927, 935, 936, 937, 45291†, 45311†, 45400†, 45445†, 45468†, 45506†, 45666†, 45701†, PAO1 | †Strains extracted from acute infected wounds. Remaining are clinical extracts from infected chronic wounds. |

LB and TSB broth were prepared in MilliQ water according to the standard protocol and immediately autoclaved after preparation. *E. coli* DH5α and *P. aeruginosa* were grown in LB while *S. aureus* was cultured in TSB. Bacteria were cultured in 10 ml of broth contained in Falcon tubes placed in a shaking incubator at 37° C. for 16 hours. The Optical Density (OD) of cultured bacteria before and after dilution was taken at 600 nm in absorbance mode. The OD of diluted bacteria was then related back to the colony-forming unit per mil (CFU/ml) by means of conventional plating and colony counting methods. The initial concentration of bacteria inoculated with vesicles was approximately $10^4$ CFU $ml^{-1}$.

Fluorescent Plate Reading Assay

A BMG Labtech fluorostar plate reading fluorimeter with a 96 well plate was used to measure the time-dependent fluorescent response of vesicles during incubation with growing bacteria at 37° C. The fluorescent response was measured with excitation and emission wavelengths of 495 nm and 520 nm respectively. A 50 µl volume of each vesicle solution was inoculated with 100 µl of diluted broth containing bacteria in each well, with six replica wells for each type of vesicle-bacteria combination in each experiment. Additionally, 100 µl of HEPES buffer and diluted Triton X-100 were also added to each vesicle type as a negative and positive control, respectively. The fluorescent response of lipid vesicles inoculated with bacteria, HEPES buffer and Triton X-100 was continuously measured for 18 hours at 37° C. For each type of vesicle-bacteria combination, the fluorescence average and standard deviation of six parallel wells was used to calculate the response with respect to the fluorescence increase at the end of each measurement.

Results and Discussion

Effect of Cholesterol and TCDA on Stability and Sensitivity of Vesicles

One of the principle differences in membrane components between eukaryotic and prokaryotic cells is the presence or absence of cholesterol. Cholesterol is the essential eukaryotic cell membrane component, comprising as much as 25% of lipids in human erythrocytes and as little as a mere trace amount in disk membrane (bovine) (Gennis, 1989). Apart from its physiological role, cholesterol in general maintains the integrity and lateral fluidity of cell membranes for the normal functioning of the cell (Henna et al., 2002, Koyama et al., 1999). Artificial lipid bilayer membranes containing cholesterol exhibit similar changes in membrane fluidity, line tension and formation of rafts, especially if the membrane contains sphingolipids (Veatch and Keller, 2005). Significantly, the cholesterol plays an important role in interactions of cell membranes with bacterial toxins, either directly or indirectly (Palmer, 2004), and its presence or absence in cell membranes influences the susceptibility of the cells to the bacterial toxins. This hypothesis was verified by designing lipid vesicles with varying cholesterol percentages, and examining the effect of cholesterol on sensitivity of vesicles to tested pathogenic bacteria. Furthermore, polymerizable lipid TCDA was incorporated in the lipid bilayer to create laterally cross-linked polymer networks within the membrane, thus enhancing the thermodynamic stability of the lipid membrane at elevated temperatures (Zhou et al., 2010). TCDA had 21 carbon atoms in a hydrophobic tail, which was shortened to 17 after lateral cross-linking by UV-light, minimizing the mismatch in chain length with DPPC and DSPC lipids. Individual and combined effects of cholesterol and TCDA on lipid bilayer stability and sensitivity were also explored.

DPPC Vesicles (Type A and B)

Studies on Type A vesicles indicated that increasing the cholesterol concentration decreased the passive leakage in Hepes buffer, but also decreased the response on addition of both P. aeruginosa and S. aureus (see FIG. 6a). The maximum response for Type A vesicles, taking minimal passive leakage into account, was exhibited by vesicles containing 20 mol % cholesterol, with around twice the response for P. aeruginosa than for S. aureus. Type B vesicles, where the photopolymerizable cross-linker TCDA was added at a fixed 25 mol % and the cholesterol concentration was varied, showed increasing stability at high cholesterol concentrations, but a notable, and almost exclusive, response to S. aureus at cholesterol concentrations of 30 mol % and above (see FIG. 6b).

DSPC Vesicles (Type C and E)

Type C vesicles, utilising the longer chain lipid DSPC, showed a greater stability than the DPPC vesicles in general, and a strong effect with respect to cholesterol concentration on the response to the different bacterial toxins, with 20 mol % cholesterol having around a 4 fold greater response to P. aeruginosa than for S. aureus (see FIG. 6c). The type E vesicles (DSPC with 25 mol % TCDA) showed a marginally greater response to S. aureus over P. aeruginosa, which became more marked at higher cholesterol concentrations (see FIG. 6d).

DSPC Vesicles (Type D)

Type D vesicles, composed of DSPC with 20% cholesterol and varying TCDA mol % (0-25%) showed minimal passive leakage in Hepes buffer and a significant increase in response to S. aureus with respect to increasing TCDA percentages, while the response to P. aeruginosa remained almost the same regardless of TCDA mol % (see FIG. 7). These results indicated that the DPPC vesicles were more sensitive to bacteria than DSPC vesicles, with an optimum observed at a 20% cholesterol concentration. In the absence of TCDA, all vesicle types showed higher response to P. aeruginosa than to S. aureus. This was not the case, however, if TCDA was included, where a relatively higher response was observed to S. aureus with increasing TCDA mol %. The reduced sensitivity of DSPC vesicles in general could be partly explained in terms of differences in the gel-liquid phase transition temperature ($T_m$): at the relatively higher $T_m$ of DSPC (55° C.) the lipid bilayer would still be in a gel phase with minimal fluidity at 37° C. This may reduce the passive leakage and most likely hinder the successful binding, and subsequent activation, of bacterial toxins onto vesicles. TCDA-dependent response to S. aureus was not fully explained, as there was no evidence of interaction between polymerizable lipids and bacterial toxins (Jelinek and Kolusheva, 2007). It is possible that the formation of a TCDA polymer network could create local domains, rich in lipids and cholesterols, which would provide pre-defined targets for local concentrations of bacterial toxins (Verdon et al., 2009). The experimental results in FIGS. 6 and 7 implied that the sensitivity of vesicles to either P. aeruginosa or S. aureus, or both, could be achieved by adjusting the percentage composition of DPPC, DSPC, cholesterol and TCDA. Three types of vesicles were chosen for the selective response tests; vesicle 6 for the detection of both bacteria, while vesicles 11 and 9 were utilised for selective detection of P. aeruginosa and S. aureus, respectively.

Selectivity to Non-Pathogenic and Pathogenic Strains

Colorimetric selection of bacteria was demonstrated using non-pathogenic E. coli DH5α and pathogenic strains of P. aeruginosa PAO1 (Winsor et al., 2009) and S. aureus MSSA 476 (Holden et al., 2004). It took on average 6 hours to observe a notable change in fluorescence with an initial bacterial mass of $10^4$ CFU $ml^{-1}$ (FIG. 8). Vesicle 6 produced a 5-10 fold higher fluorescent response to both P. aeruginosa and S. aureus relative to negative controls in Hepes buffer and E. coli DH5α (FIG. 8a). Further selection between two pathogenic strains was illustrated in FIGS. 8b and 8c; with vesicle 11 only responding to PAO1 strain of P. aeruginosa while vesicle 9 only selected for the MSSA 476 strain of S. aureus. This selectivity can be explained with respect to the lipid formulation of vesicles: lipid availability and membrane fluidity as well as the toxins involved with pathogenic bacteria. It has been shown that the activities of PFTs of *S. aureus* increased with an increase in membrane fluidity, most especially in membranes containing lipids of shorter acyl chains (Potrich et al., 2009). Vesicle 6, comprised of DPPC, cholesterol and TCDA, maintained a higher membrane fluidity, especially at 37° C., to promote nonspecific binding of toxins with lipids in the fluid membrane, thus providing sensitivity to both tested pathogens. Using only DSPC and cholesterol, the membrane fluidity of vesicle 11 was shifted partly into a gel-like phase at 37° C., making toxins of *S. aureus* incompatible with the relatively stiff membrane. *P. aeruginosa*, however, seemed unaffected by the low membrane fluidity, as evidenced in FIG. 8*b*, most likely due to the associated toxins and their modes of action. *P. aeruginosa* secrete lipid degradable enzymes, such as phospholipase C, which targets and hydrolyses the phosphate head group of phospholipids (Songer 1997; Titball, 1993). Such toxins require only the lipid head group availability, without being dependent on membrane fluidity for their activation. Thus vesicle 11, which was rich in DSPC lipids, possibly became the target for, and thus relatively sensitive to, *P. aeruginosa*.

Vesicle 9, composed of 50% cholesterol and 25% TCDA, with the remaining 25% made up of DPPC and DPPE (see in table 1), could form the raft-like domains coexisting alongside with the lipid-rich domains within the membrane (Garcia-Saez and Schwille, 2010; Mateo et al., 1995). The liquid-ordered state of cholesterol-rich domains could possibly give rise to higher concentration of *S. aureus* toxins and their activities in remaining DPPC lipid-rich liquid-disordered domains at 37° C. *P. aeruginosa*, however, primarily required lipids to activate most of its lipid-degrading enzymes. With the minimal lipid composition in vesicle 9, activation of *P. aeruginosa* toxins in lipid membranes mostly dominated by cholesterol and TCDA was expected to be minimal or ineffective, resulting in the increased selectivity of vesicle 9 to *S. aureus* (FIG. 8*c*). The relative fluorescence response of the vesicles to the bacteria and Hepes buffer was plotted in FIG. 8*d*, and the visible colorimetric selection with respect to *E. coli* DH5α, *P. aeruginosa* PAO1 and *S. aureus* MSSA 476, using three types of vesicles, was illustrated in FIG. 9.

Selective Sensitivity Between 40 Strains of *P. aeruginosa* and *S. aureus*

In order to evaluate the sensitivity and the selectivity over a range of pathogenic strains, three selected vesicles were tested against 40 additional strains (20 each) of *S. aureus* and *P. aeruginosa*, extracted from wounds with known infections. Experimental procedure was as described above. The fluorescence and absorbance of the three replicates of each vesicle-bacterium combinations were measured at the start and the end of each experiment, and the results were plotted in FIGS. 10*a* and 10*b* for *P. aeruginosa* and *S. aureus*, respectively. Vesicle 11 showed positive responses to all the *P. aeruginosa* strains, with the exception of strains 856 and 887 (FIG. 10). Absorbance data indicated that strains 856 and 887 did not grow during the experiment; consequently the positive responses were not shown, in contrast to the remaining tested strains. The reason for suppressed growth of strains 856 and 887 was not clear, despite the fact that all the strains of *P. aeruginosa* grew well in Falcon tubes. It is possible that the growth condition of these particular strains in 96 wells plate may not be optimum to support the toxin expression, and subsequently no lysis of vesicles was observed. Selectivity of vesicle II over vesicle 9 in terms of the increment in fluorescence intensity was observed as a 2-6 fold increase (FIG. 10*a*), which was clearly distinguishable when observed under UV light.

Interestingly, all 20 strains of *S. aureus* showed higher response to vesicle 9 than to vesicle 11 (FIG. 10*b*). A two to ten-fold increase in fluorescence with respect to vesicle 9 against vesicle 11 was clearly observed, and all tested strains of *S. aureus* grew well in the experiment, according to absorbance data. In terms of fluorescence signal strength, responses of vesicle 9 to *S. aureus* were slightly less than those of vesicle 11 to *P. aeruginosa*. This relatively low fluorescence "switch on" could be due to the particular involvement of toxins secreted by the strains of *S. aureus*, which may not necessarily lyse the vesicles completely. If this was the case, it implies that the toxins associated with *P. aeruginosa* in general have a relatively stronger lipolytic action than those produced by *S. aureus*. Nevertheless, visible and selective responses of vesicle 9 against vesicle 11 to all strains of *S. aureus* were clearly observed. It was evidenced according to the experiments that 90% of all *P. aeruginosa* strains and 100% of all *S. aureus* strains were selectively distinguished one from the other.

Conclusions

We demonstrated the selective detection between non-pathogenic bacteria *E. coli* DH5α and pathogenic strains of *S. aureus* MSSA 476 and *P. aeruginosa* PAO1 using lipid vesicles containing carboxyfluorescein dyes. There was a clear, visual selection between pathogenic and non-pathogenic strains of bacteria in the form of fluorescence colour change; switching from relatively pale to a bright green colour, after inoculation of bacteria with lipid vesicles and incubation at 37° C. More importantly, by formulating the appropriate compositions of lipids, cholesterol and polymerizable lipids, the vesicles showed further selective discrimination between two pathogenic strains of *P. aeruginosa* and *S. aureus*. Additionally, selectivity over a wide range of two common pathogenic species was demonstrated using 40 clinical strains of *P. aeruginosa* and *S. aureus*. 90% of *P. aeruginosa* strains and all of *S. aureus* strains were selectively distinguished, with visible fluorescence colour change, with two to ten-fold responses relative to each other. By integrating self-responsive lipid vesicles within a wound dressing, we believe that the current selective and discriminative sensing system has the potential for future use as an indicator of wound infection, without requiring the removal of the wound dressing throughout the wound healing process.

Acknowledgement

We would like to thank Professor Mark C. Enright (AmpliPhi Biosciences Corporation, Bedfordshire, UK), Southmead Hospital (Bristol, UK) and John Radcliffe Hospital (Oxford, UK) for the supply of bacteria. We also acknowledge the European Commission's 7$^{th}$ Framework programme for funding via the EC-FP7 consortium project no. 245500 Bacteriosafe.

REFERENCES

Arpigny, J. L., Jaeger, K. E., 1999. Biochem. J. 343, 177-183

Bailey, C. J., Redpath, M. B., 1992. Biochem. J. 284, 177-180

Branski, L. K. et al., 2009. Surg. Infec. (Larchmt) 10, 389-397

Church, D. et al., 2006. Clin. Microbiol. Rev. 19, 403-434

Dinges, M. M. et al., 2000, Clin. Microbiol. Rev. 13, 16-34

FDA: Guidance for Industry (Chronic Cutaenous Ulcer and Burn Wounds—Developing Products for Treatment) June (2006)

Garcia-Saez, Schwille, P., 2010. FEBS Lett. 584, 1653-1658
Gennis, R. B., 1989. Biomembranes: molecular structure and function, Springer-Verlag, New York.
Geny B. and Popoff, M. R. *Biology of the Cell* 98 (2006) 667-678
Gilbert, R. J. C., *Cellular and Molecular Life Sciences* 59 (2002) 832-844
Hanahan, D., 1985. DNA Cloning (A practical approach). Vol. 1, IRL Press, Oxford, UK
Henna, O-.R. et al., 2002. Prog. In Lip. Res. 41, 66-97
Hildebrand, A. et al., The Journal of Biological Chemistry 266 (1991) 17195-17200
Holden, M. T. G. et al., 2004. Proc. Nat. Mad. Sci. USA. 101, 9786-9791
Jelinek, R., Kolusheva, S., 2007. Top. Curr. Chem. 277, 155-180
Jenkins, A. T. A. et al., 2011. Burns 37S, S5
Jenkins, A. T. A., Young, A., 2010. Expe. Rev. of Anti-inf. Thera. 8, 1063-1065
Jones, V. E., 2006. Wounds UK 2, 66-73
Sir Ian Kennedy, Department of Health Publication, Review (2010)
Koyama, T. M. et al., 1999. The Chem. Edu. 4, 12-15
Laabei, M. et al., 2012. Pedia. Infect. Dis. J. 31, e73-e77
Liu, R V., 1974. The. J. of Infec. Disea. 130, S94-S99
Liu, S., et al., 2005. Langmuir 21, 8572-8575.
Mateo, C. R. et al., 1995. Biophys. J. 68, 978-987
National Burn Care Review (2001)
Palmer, M., 2004. FEMS Microbiol. Lett, 238, 281-289
Parish, C. R. Immunology and Cell Biology 77 (1999) 499-508
Parker, M. W., and Feil, S. C., Progress in Biophysics and Molecular Biology 88 (2005) 91-142
Peacock, S. J. et al., 2002. Infec. and Immu. 70, 4987-4996
Poon, V. K. M. and Burd, A. Burns 30 (2004) 140-147
Potrich, C. et al., 2009. J. Membrane Biol. 227, 13-24
Song, L. et al., 1996. Science 274, 1859-1866
Songer, J. G., 1997. Tren. in Microbiol. 5, 156-161
Tangpraphaphorn, S., 2004. Open. Compu. Fac., Uni. of California at Berkeley. PM527
Titball, R. W., 1993. Microbiol. Rev. 57, 347-366
Thet, N. T. et al., 2011. Biosens. and Bioelec. 28, 227-231
Thet, N. T., Jenkins, A. T. A., 2010. Electrochem. Comm. 12, 1411-1415
Tseng, C. W. et al., 2009. PLoS ONE, 4, e6387, 1-10
UK Burn Injury Data (1986-2007)
Veatch, S. L., Keller, S. L., 2005. Biochim. et Biophys. Act. 1746, 172-185
Verdon, J. et al., 2009. Peptides 30, 817-823
Wasiak, J. et al., Cochrane Database of Systematic Reviews 2 (2009) 1-51
Winsor, G. L. et al., 2009. Nucl. Aci. Res. 37, D483-D488
Young, A. E., Thornton, K. L., 2007. Arch. Dise. Childh. Edu. Pract. Ed. 92, ep97-ep100
Zhou, J. et al., 2011. Biosens. and Bioelec. 30, 67-72

The invention claimed is:

1. A method of diagnosing an infection with a pathogenic bacterial stain from a *S. aureus* strain or a *P. aeruginosa* strain, comprising
   a) contacting the infected area with a lipid bilayer vesicle comprising 1,2-dipalmitoyl-sn-glycero-3-phosphocholine (DPPC), 1,2-dipalmitoyl-sn-glycero-3-phosphoethanolamine (DPPE), and a sterol, wherein the lipid bilayer vesicle comprises between 40 and 65% DPPC and DPPE, and said lipid bilayer vesicle encapsulating a signaling molecule, wherein upon contact, said pathogenic bacterial strain lyses the lipid bilayer vesicle to releasing the signaling molecule from said lysed lipid bilayer vesicle;
   b) producing a visualizable colorimetric or fluorescent signal from said released signaling molecule, thereby indicating the presence of an infection; and,
   c) detecting said visualizable colorimetric or fluorescent signal.

2. The method of claim 1, wherein said vesicle further comprises 10, 12-tricosadiynoic acid (TCDA).

3. The method of claim 1, wherein said vesicle further encapsulates a biologically active molecule.

4. The method of claim 3, wherein said biologically active molecule is an antibiotic, an antimicrobial or a bacteriophage.

5. The method of claim 1, wherein said signaling molecule is fluorescent or non-fluorescent dye.

6. The method of claim 5, wherein said signaling molecule is a fluorescein, crystal violet, bromothymol blue, methyl orange or calcein.

* * * * *